(12) United States Patent
McCoy

(10) Patent No.: US 11,918,619 B1
(45) Date of Patent: Mar. 5, 2024

(54) INDIVIDUAL DOSING OF CANNABIS AND TOBACCO FOR STANDARDIZATION AND CONTROL

(71) Applicant: David McCoy, Defuniak Springs, FL (US)

(72) Inventor: David McCoy, Defuniak Springs, FL (US)

(*) Notice: Subject to any disclaimer, the term of this patent is extended or adjusted under 35 U.S.C. 154(b) by 0 days.

(21) Appl. No.: 18/072,744

(22) Filed: Dec. 1, 2022

(51) Int. Cl.
| | |
|---|---|
| *A61K 36/81* | (2006.01) |
| *A61J 3/10* | (2006.01) |
| *A61K 36/185* | (2006.01) |
| *A61K 31/352* | (2006.01) |
| *A61K 31/05* | (2006.01) |
| *A61K 9/48* | (2006.01) |
| *A61K 9/20* | (2006.01) |
| *A61J 3/07* | (2006.01) |
| *A24D 1/18* | (2006.01) |
| *A24D 1/00* | (2020.01) |
| *A24D 1/04* | (2006.01) |
| *B65D 75/36* | (2006.01) |
| *A61K 9/24* | (2006.01) |

(52) U.S. Cl.
CPC .............. *A61K 36/81* (2013.01); *A24D 1/002* (2013.01); *A24D 1/045* (2013.01); *A24D 1/18* (2013.01); *A61J 3/07* (2013.01); *A61J 3/10* (2013.01); *A61K 9/209* (2013.01); *A61K 9/2095* (2013.01); *A61K 9/4808* (2013.01); *A61K 31/05* (2013.01); *A61K 31/352* (2013.01); *A61K 36/185* (2013.01); *B65D 75/36* (2013.01); *B65D 2203/02* (2013.01)

(58) Field of Classification Search
None
See application file for complete search history.

(56) References Cited

FOREIGN PATENT DOCUMENTS

EP          0964093 A1 * 12/1999

\* cited by examiner

*Primary Examiner* — Michael V Meller
(74) *Attorney, Agent, or Firm* — Georgiy L. Khayet

(57) ABSTRACT

Provided are therapeutic products in a form of individual doses for consumption by users. A therapeutic product includes a therapeutic portion and a package. The therapeutic portion includes one or more parts of a plant and may be compressed and formed into an individual dose. The therapeutic product further includes a fibrous portion that includes one or more further parts of the plant. The fibrous portion is structurally attached to the therapeutic portion to form the individual dose of the therapeutic product. The package accommodates the therapeutic portion and the fibrous portion acting as a structural substrate, or the therapeutic portion alone without the fibrous portion.

1 Claim, 8 Drawing Sheets

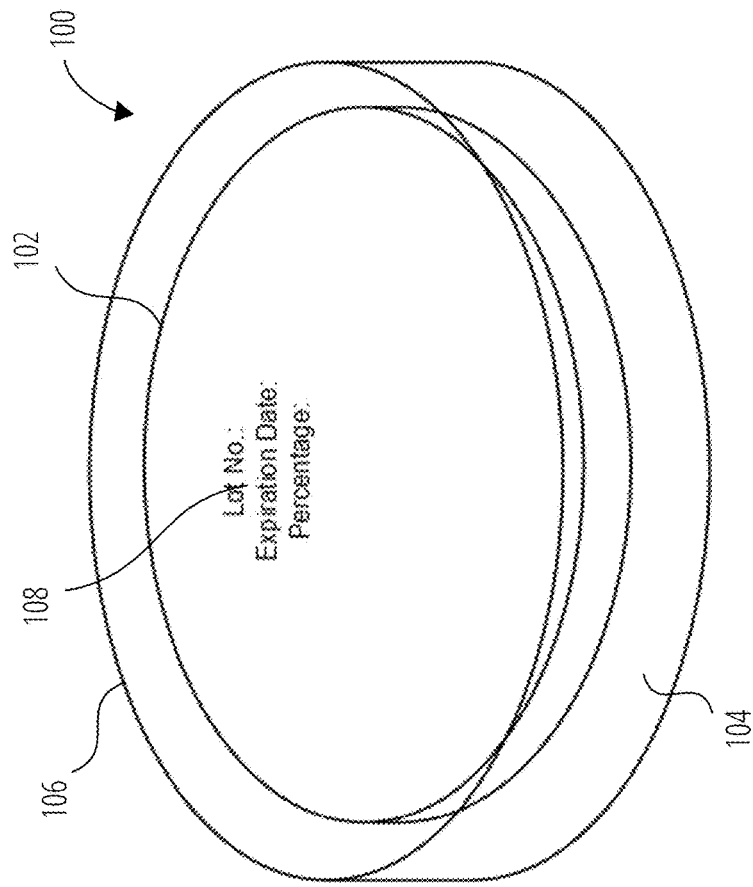
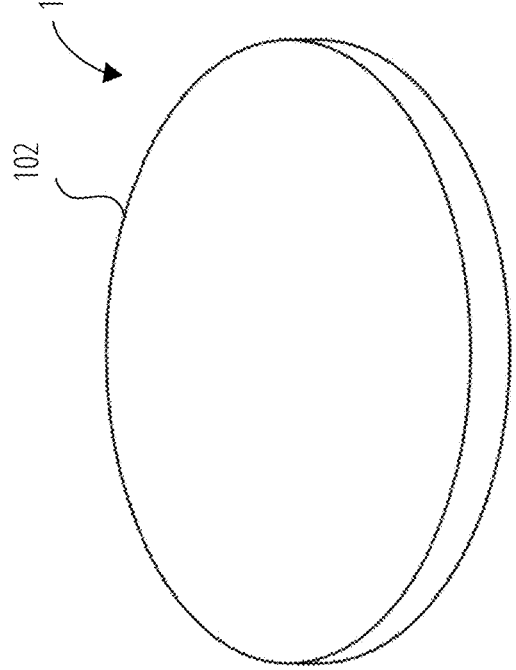
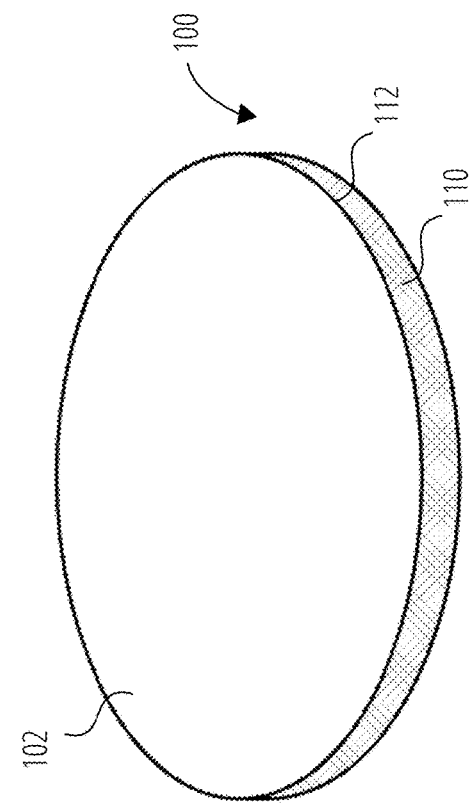
FIG. 1B
FIG. 1A
FIG. 1C

INDIVIDUAL DOSING OF CANNABIS AND TOBACCO FOR STANDARDIZATION AND CONTROL

TECHNICAL FIELD

This disclosure relates to providing individual dosing of cannabis and/or tobacco for standardization and control. Specifically, this disclosure relates to cannabis-based therapeutic products and/or tobacco (nicotine)-based products in a form of an individual dose for user consumption.

BACKGROUND

A large portion of the tobacco and cannabis consuming public prefers to consume, by smoking and/or vaporizing, processed natural leaf-based products. It is acknowledged that many users have opted to ingest nicotine and therapeutic agents found in cannabis by vaporization and inhalation of a liquefied form via a vape pen, but this method generally turns a liquid into an aerosol, which is inhaled into the lungs and then coalesces back into a liquid. This cumulative effect is similar to drowning and has been shown to be more detrimental than inhaling smoke or a vaporized form of the leaf product. Thus, manufacturers of tobacco- and cannabis-based products intended for smoking, vaporizing, or inhaling in a liquefied form need to make efforts to assure that the contents and strength of the material containing the therapeutic agent in the tobacco- and cannabis-based products is measured, regulated, and safe for users.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

Generally, the present disclosure is directed to therapeutic products in the form of individual doses for consumption by users. According to one example embodiment of the present disclosure, a therapeutic product in a form of an individual dose for consumption is provided. The therapeutic product may include a therapeutic portion and a package for accommodating the therapeutic portion. The therapeutic portion may include one or more parts of a plant and may be compressed and formed into an individual dose.

According to another example embodiment of the present disclosure, a method for producing a therapeutic product in the form of an individual dose for consumption is provided. The method may commence with separating a plant into one or more parts of the plant and one or more further parts of the plant. The method may further include reducing one or more parts of the plant in size to provide a therapeutic portion and compressing the therapeutic portion to provide the therapeutic portion in a compressed form. The method may proceed with forming the therapeutic portion in the compressed form via at least one of a die cutter and a mold to provide the individual dose of the therapeutic portion.

Other example embodiments of the disclosure and aspects will become apparent from the following description taken in conjunction with the following drawings.

BRIEF DESCRIPTION OF DRAWINGS

Exemplary embodiments are illustrated by way of example and not limitation in the figures of the accompanying drawings, in which like references indicate similar elements.

FIG. 1A illustrates a therapeutic product that includes a therapeutic portion, according to an example embodiment.

FIG. 1B illustrates a therapeutic product that includes a therapeutic portion and a package, according to an example embodiment.

FIG. 1C illustrates a therapeutic product that includes a therapeutic portion and a fibrous portion, according to an example embodiment.

DETAILED DESCRIPTION

Figure 2:
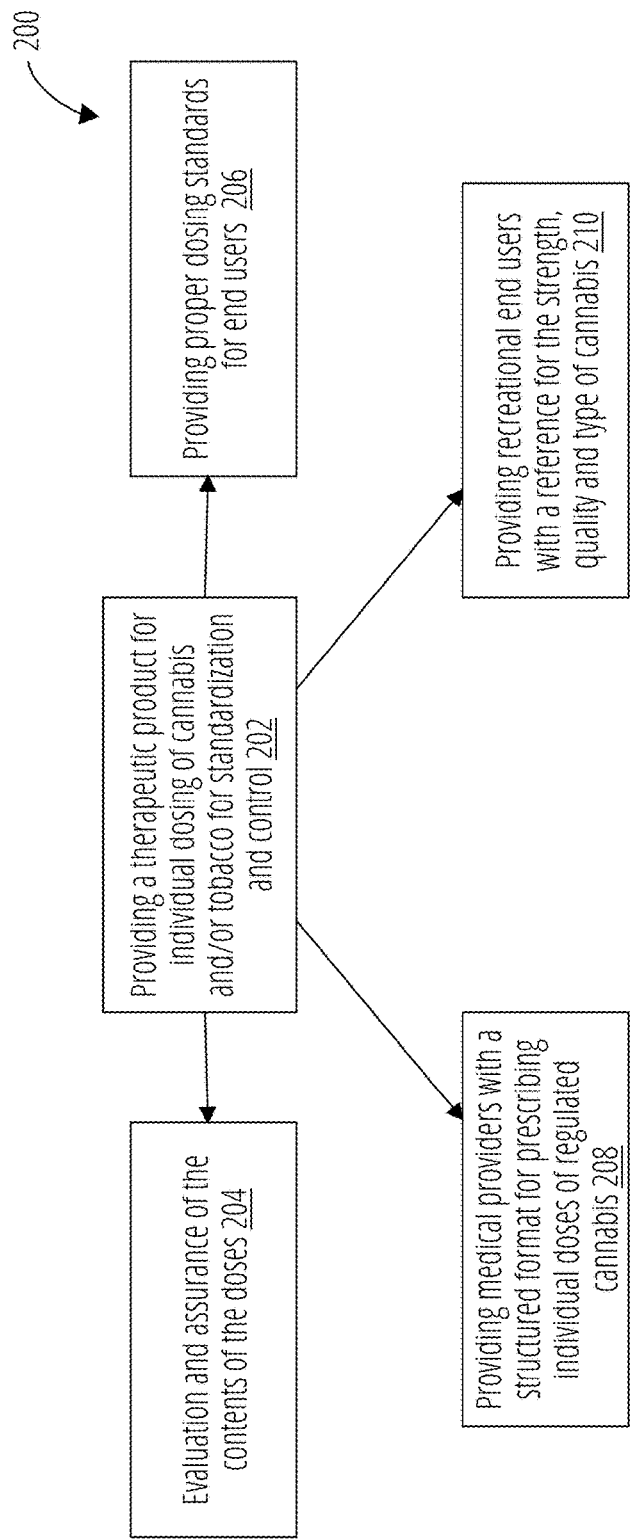
FIG. 2 is a schematic diagram illustrating advantages of providing a therapeutic product for individual dosing of cannabis and/or tobacco for standardization and control, according to an example embodiment.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and operational changes can be made without departing from the scope of what is claimed. The following detailed description is, therefore, not to be taken in a limiting sense, and the scope is defined by the appended claims and their equivalents.

Generally, the embodiments of this disclosure relate to handling, manufacturing, packaging, and labeling of individual and multi-pack doses or servings of a processed natural leaf material of tobacco and/or cannabis. The disclosure relates to a therapeutic product in a form of an individual dose for consumption by users by eating, smoking, or vaporizing. The therapeutic product may include a therapeutic portion and a package. The therapeutic portion may include one or more parts of a plant and may be compressed and formed into an individual dose. The therapeutic product may further optionally include a fibrous portion that may include one or more further parts of the plant. The fibrous portion may be structurally attached to the therapeutic portion to form the individual dose of the therapeutic product. The package may accommodate the therapeutic portion and the fibrous portion that acts as a structural substrate for the therapeutic portion. In an example embodiment, the package may accommodate the therapeutic portion only, without the fibrous portion.

Referring now to the drawings, various embodiments are described in which like reference numerals represent like parts and assemblies throughout the several views. It should be noted that the reference to various embodiments does not limit the scope of the claims attached hereto. Additionally, any examples outlined in this specification are not intended to be limiting and merely set forth some of the many possible embodiments for the appended claims.

FIG. 1A illustrates a therapeutic product 100, according to an example embodiment. The therapeutic product 100 can be provided as an individual dose for consumption. The therapeutic product 100 may include a therapeutic portion 102. The therapeutic portion 102 may include one or more parts of a plant. In an example embodiment, the plant may include cannabis, tobacco, and a combination of cannabis and tobacco. The therapeutic portion 102 may be compressed and formed as an individual dose. The one or more parts of the plant may include parts that contain resins rich in therapeutic agents, such as tetrahydrocannabinol (THC), cannabidiol (CBD), and so forth, or nicotine. Therefore, the one or more parts of the plant are parts that may include THC, CBD, other therapeutic agents, or nicotine. Therefore, therapeutic portion 102 may include a purely resinous individual dose containing therapeutic agents.

FIG. 1B illustrates a therapeutic product 100, according to an example embodiment. The therapeutic product 100 may include a therapeutic portion 102 and a package 104 for accommodating the therapeutic portion 102. The therapeutic portion 102 may include one or more parts of a plant. In an example embodiment, the plant may include cannabis, tobacco, and a combination of cannabis and tobacco. In an example embodiment, the one or more parts of the plant used for therapeutic portion 102 may include flowers and leaves of the plant. The goal is to harvest the resins that are rich in therapeutic agents (e.g., THC resins) and are present in the flowers and leaves and use the resins in therapeutic portion 102.

The therapeutic portion 102 may be compressed and formed into the individual dose 106. The package 104 may be marked with one or more markings 108. The marking 108 may include one or more of the following: a lot number of the therapeutic product 100, an expiration date of the therapeutic product 100, a note for a user of the therapeutic product 100, a warning for a user of the therapeutic product 100, a dosage of the therapeutic portion 102 in the therapeutic product 100, a strength of the therapeutic portion 102 in the therapeutic product 100, a type of the therapeutic portion 102, a percentage of the therapeutic portion 102 in the therapeutic product 100, and so forth. Thus, each separate package 104 containing the individual doses 106 may be marked with, e.g., a lot number, expiration/"best by" date, strength of a therapeutic agent in a form of the percentage of active ingredients, i.e., THC, CBD, and so forth. The package 104 may be a mechanism for delivery of an integrated mass production and distribution system for dispensing measured and controlled dosages of medical and/or recreational cannabis and cannabis derivative products into devices available on the market.

Package 104 may be made of a non-transparent, semi-transparent, or transparent material. In FIG. 1B, package 104 is made of a transparent material and the therapeutic portion 102 can be seen through package 104. Package 104 may be made of any material applicable for packaging the therapeutic portion 102, such as a plastic material, paper, hemp, hemp cigarette paper, combinations of any of the plastic material, paper, hemp, and hemp cigarette paper, and so forth. The shape and type of package 104 may be selected so as to accommodate the therapeutic portion 102. In an example embodiment, upon placing therapeutic portion 102 into package 104, the package 104 may be sealed to prevent moisture and odor from exiting and entering the package 104.

FIG. 1C illustrates a therapeutic product 100, according to an example embodiment. The therapeutic product 100 can be provided as an individual dose for consumption. The therapeutic product 100 may include a therapeutic portion 102 and a fibrous portion 110.

The therapeutic portion 102 may include one or more parts of a plant that include THC, CBD, and other therapeutic agents. The fibrous portion 402 may include one or more further parts of a plant. The one or more further parts of the plant may include a stem and branches of the plant.

As shown in FIG. 1C, the therapeutic portion 102 may be provided in the form of a substrate of a predetermined thickness and a predetermined shape (e.g., in a pancake-like form). In an example embodiment, the fibrous portion 110 may be provided in the form of a fibrous sheet of a predetermined thickness and a predetermined length. The fibrous portion 110 may be attached to the therapeutic portion 102 around a circumference 112 of the therapeutic portion 102. Specifically, the therapeutic portion 102 may be enclosed/restrained by the fibrous portion 110 around the circumference 112 of the therapeutic portion 102.

FIG. 2 is a schematic diagram 200 illustrating advantages of providing a therapeutic product for individual dosing of cannabis and/or tobacco for standardization and control, according to an example embodiment. The providing of a therapeutic product for individual dosing of cannabis and/or tobacco shown in block 202.

One of the reasons for the importance of standardization and control when providing the therapeutic product for individual dosing of cannabis and/or tobacco shown in block 202 includes evaluation and assurance of the contents of the doses, as shown in block 204. The importance of assuring the contents and strength of the material containing the therapeutic agent cannot be understated. For medical prescribers, this becomes a standard for prescriptions, dosing, and quality assurance. Additionally, there have been instances where chemical adulterants, such as fentanyl (a potent synthetic opioid), have been found in unregulated cannabis. Use of these types of uncontrolled marijuana laced with fentanyl has resulted in death of the unknowing user.

Other types of chemicals found in uncontrolled marijuana include defoliants, such as paraquat, and herbicidal dioxin contaminants commonly found in Agent Orange (a chemical herbicide and defoliant).

As shown in block 206, another advantage of standardization and control when providing the therapeutic product for individual dosing of cannabis and/or tobacco is providing proper dosing standards for end users. Dosing recommendations are important for end users who are unfamiliar with consuming cannabis products or smoking and vaporizing materials containing a therapeutic agent.

Block 208 shows one more advantage of standardization and control of providing the therapeutic product for individual dosing of cannabis and/or tobacco, which includes providing medical providers with a structured format for prescribing individual doses of regulated cannabis. Dosing recommendations are important for medical providers who may be unfamiliar with prescribing or recommending this type of therapeutic agent and may provide specific dosing and frequency guidelines.

As shown in block 210, one more advantage of standardization and control when providing the therapeutic product for individual dosing of cannabis and/or tobacco is providing recreational cannabis users 306 with a reference to the strength, quality, and type of cannabis. Recreational cannabis users can benefit from a selection of multiple variants of cannabis products based on the type, strength, flavors and desired effects.

Figure 3:
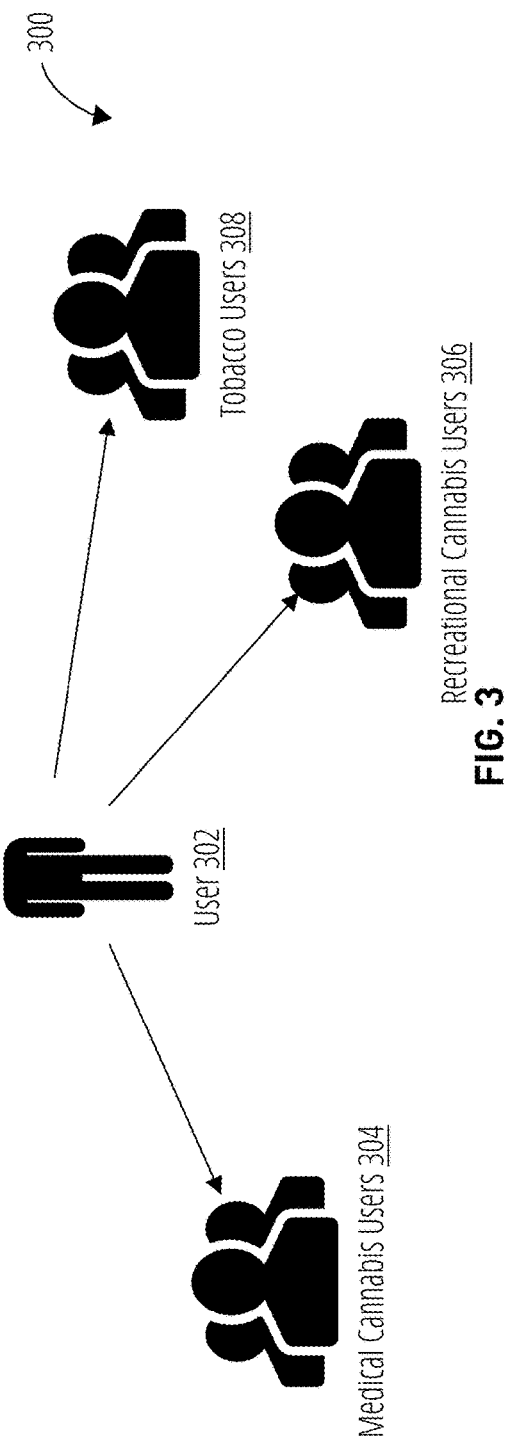
FIG. 3 is a schematic diagram illustrating a user of a therapeutic product in the form of an individual dose, according to an example embodiment.

FIG. 3 is a schematic diagram 300 illustrating an example user 302 of a therapeutic product in the form of an individual dose. The contents and/or the package of the therapeutic product may differ for each group of users.

The first group of users is medical cannabis users 304. The medical cannabis users 304 may include medical patients who have been prescribed cannabis by their healthcare providers. For the medical cannabis users 304, a package of the therapeutic product may be in accordance with U.S. Food and Drug Administration (FDA) approved packaging requirements for notes, cautions, warnings, dosing, strength, type, and percentage of therapeutic agents in the therapeutic product.

The second group of users is recreational cannabis users 306. The recreational cannabis users 306 may include users who prefer a purely cannabis product, a cannabis and tobacco mixture, and flavored cannabis and/or tobacco mixtures. For the recreational cannabis users 306, the package of the therapeutic product may be designed to promote the features, advantages, and benefits of the various choices of cannabis, flavored cannabis, cannabis and tobacco mixtures, and flavored cannabis and tobacco mixtures.

The third group of users includes tobacco users 308, who are users of tobacco and tobacco derivatives, in particular, nicotine. For anyone who has ever smoked a cigarette, it is commonly understood that the best "drag" off of a cigarette is the first drag because it is the "coolest" and provides the best tobacco "taste." Every drag after the first drag is hot and tasteless. The reason for this is in the physical characteristics of the burning cigarette. Essentially there is a paper tube filled with tobacco and the standard commercial additives in the middle. At one end of the tube, there is a synthetic cellulose filter and at the other end of the tube there is a combustion source. During the first drag, the heat from the combustion source is pulled by vacuum over the tobacco material in the tube. As the heat moves further away from the combustion source, the temperature lowers enough so that combustion ceases and vaporization of the tobacco in the tube commences. That vaporized tobacco is what provides the "flavor" of the tobacco, but it can only be vaporized once, during the first "drag." After the first drag, the tobacco available for vaporization has been consumed and all the rest of the remaining cigarette is combusted by the burning ember at the end of the tube. Although some remaining nicotine is consumed, the majority of the nicotine is gone and the smoker is consuming an inert material.

As the therapeutic product of the present disclosure is provided in a form of an individual dose and can serve as a recreational product in some example embodiments, the therapeutic product can be consumed by using an "individual serving" method of consuming tobacco. With this method, all the tobacco is vaporized from the therapeutic product during the one and only "drag" of the user from an end user device. This method enables the user to receive a cooler (lower temperature) serving and receive all of the tobacco flavor and none of the burnt, tasteless high temperature smoke. Thereby, using this method of consumption of the therapeutic product, "every drag is the first drag." Thus, the therapeutic product maximizes efficiencies in nicotine consumption, reduces the amount of smoking/vaporization cycles by the user, omits consuming a hot, tasteless "inert" material by the user, and reduces exposure of the user to carcinogenic compounds.

Thus, the therapeutic product in a form of the individual dose provides the single-dose, individual serving method of consumption for cannabis, tobacco, and cannabis and tobacco mixed products, which improves user experience by maximizing the flavor of the product, reduces the user exposure to carcinogenic compounds by reducing the overall consumption of non-therapeutic compounds by the user, reduces the overall amount of product consumed, reduces emitted second hand smoke by 99%, and reduces greenhouse gas contributions. Moreover, the therapeutic product in a form of the individual dose provides the single-dose, individual serving method of consumption for cannabis, tobacco, and cannabis and tobacco mixed products, which enables the user to reduce his individual contribution to global warming when used with a commercially available lighter-less device.

Figure 4:
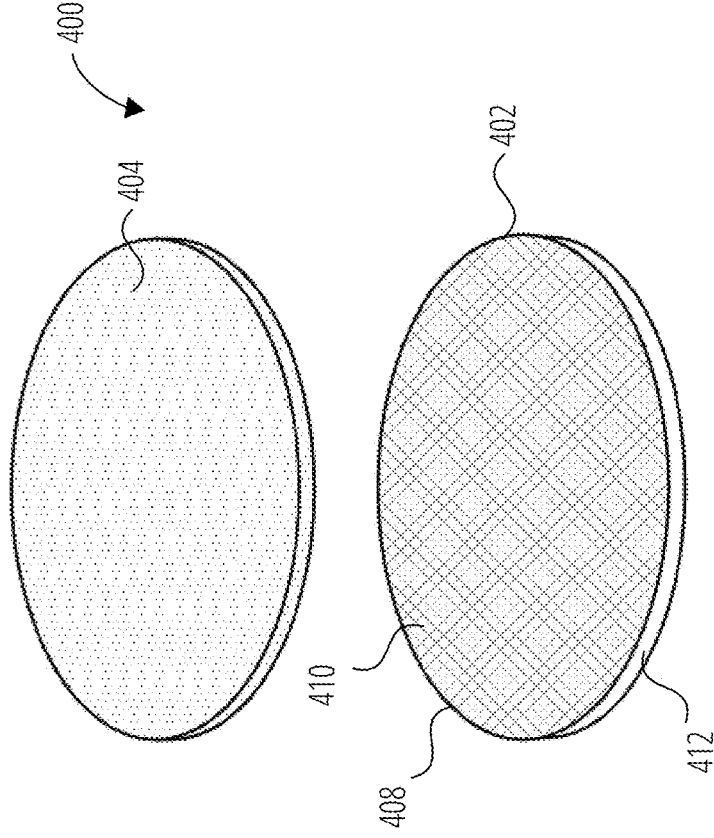
FIG. 4 illustrates components of a therapeutic product that includes a therapeutic portion and a fibrous portion, according to an example embodiment.

FIG. 4 illustrates components of a therapeutic product 400, according to an example embodiment. The therapeutic product 400 may include a fibrous portion 402. The fibrous portion 402 may include one or more further parts of a plant. The one or more further parts of the plant may include a stem and branches of the plant. In an example embodiment, the stem and branches may include hemp. As used herein, the term "hemp" refers to all portions of the plant that are non-psychoactive. Because the stem and the branches that constitute the fibrous portion 402 contain no psychoactive agents, the fibrous portion 402 is the non-psychoactive portion of the plant and may be referred to herein as "hemp." The word "hemp" refers to the same species and genus of a plant (e.g., cannabis) but includes only portions that do not contain psychoactive agents or THC.

The fibrous portion 402 may be compressed into a form applicable for providing an individual dose. An example form may include round, oval, rectangular, circular, elliptic, and so forth. In an example embodiment, the fibrous portion 402 may include a substrate forming a structural lattice for attachment of the therapeutic portion. An example substrate is shown as a woven substrate 408. The woven substrate 408 may have a top surface 410 and a bottom surface 412.

The therapeutic product 400 may further include a therapeutic portion. The therapeutic portion may include one or more parts of the plant. The one or more parts of the plant may include the resinous flowers and leaves of the plant. The therapeutic portion may include a first subportion 404 of the therapeutic portion configured to be attached to the top surface 410 of the woven substrate 408. The therapeutic portion may further include a second subportion 406 of the therapeutic portion configured to be attached to the bottom surface 412 of the woven substrate.

The fibrous portion 402 and the therapeutic portion (the first subportion 404 and the second subportion 406) may be compressed into a form applicable for providing an individual dose. In an example embodiment, the selected form of the fibrous portion 402 and the therapeutic portion may be applicable for using the therapeutic product 400 in devices for smoking/vaporization available on the market.

Figure 5:
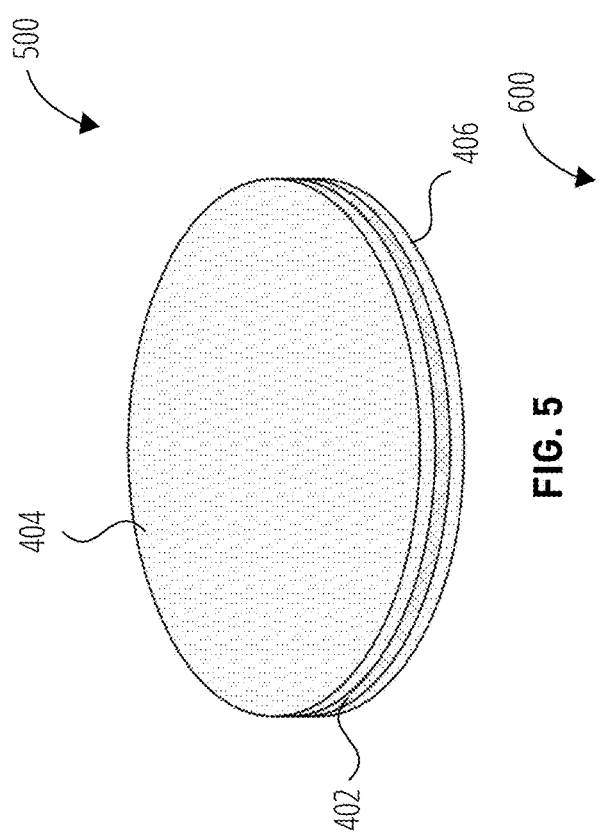
FIG. 5 illustrates a therapeutic product, in which a therapeutic portion and a fibrous portion are connected to each other, according to an example embodiment.

FIG. 5 illustrates a therapeutic product 500, in which a therapeutic portion and a fibrous portion are connected to each other, according to an example embodiment. The first subportion 404 and the second subportion 406 of the therapeutic portion may be structurally attached to the fibrous portion 402 to form the individual dose of the therapeutic product 500.

In an example embodiment, the plant used for providing the therapeutic product 500 may be selected from cannabis, tobacco, and a combination of cannabis and tobacco. In some example embodiments, the therapeutic product 500 may further include one or more flavoring additives to flavor the combination of cannabis and tobacco. The one or more flavoring additives may be added to any of the therapeutic portion and the fibrous portion. In some example embodiments, the therapeutic product 500 may further include further additives applicable for adding to the therapeutic product 500.

In the embodiment shown in FIG. 5, the therapeutic portion (the first subportion 404 and the second subportion 406) may be structurally attached to the fibrous portion 402 to form an individual dose in the form of a tablet or a capsule.

The dimensions of the therapeutically measured, regulated, and structurally self-supported individual doses of the therapeutic product 500 may be selected to enable the individual doses to be used in any of commercially available smoking or vaporization devices present on the market. The size of the individual doses may depend on the strength or concentration of the therapeutic agents present in the therapeutic product. Examples of light, regular, or extra strength doses may be as follows: 0.300 inches wide×0.145 inches tall, 0.400 inches wide×0.170 inches tall, and 0.450 inches wide×0.260 inches tall, respectively. The ratio of fibrous binding agents constituting the fibrous portion and therapeutic agents constituting the therapeutic portion can also be dependent upon the relative strength of the therapeutic agents used during manufacturing of the therapeutic product.

As used herein, the term "regulated doses" means pharmaceutical doses of the therapeutic material (e.g., cannabis) approved by guidelines for pharmaceutical prescribing to users. For example, the regulated dose may include 3 mg of THC or CBD, 12 mg of THC or CBD, or 26 mg of THC or CBD, and may be prescribed to a user depending on a particular dosage required for the user. The weight of the therapeutic portion and the weight of the fibrous portion in the therapeutic product may be selected based on predetermined criteria.

As used herein, the term "therapeutically measured doses" means pharmaceutical doses of the therapeutic material (e.g., cannabis) approved for prescribing for a particular health condition of a user. The therapeutically measured doses may be marked, for example, by a percentage of a therapeutic agent in the therapeutic product, e.g., 4% of THC, 12% of THC, and so forth.

In some embodiments, the relative strength may mean a percentage of the therapeutic agent per a mass unit of the therapeutic product, e.g., 18% THC or CBD in 3 mg therapeutic product for "strong/heavy" individual doses, 12% THC or CBD in 3 mg therapeutic product for "regular" individual doses, 4% THC or CBD in 3 mg therapeutic product for "light" individual doses, and so forth.

The therapeutic agents constituting the therapeutic portion can be tested for the relative strength (percentage of psychoactive ingredients (variations of THC, CBD, and so forth), or, in some embodiments, for the strength of the nicotine) so proportional amounts of the therapeutic agent and the binding agent may be regulated to produce a repeatable, uniform, and expectable dose of the therapeutic agent in the therapeutic product. In an example embodiment, the end state of the individual doses, i.e., the form and content of the therapeutic agents presented for consumption, may be not dependent on the method of manufacture of the individual doses.

The method of testing the relative strength of the cannabis and/or tobacco may include any of the commercially available methods of measuring chemical agents, such as mass spectroscopy and high performance liquid chromatography. Once the concentrations of active therapeutic agents are determined, a method for producing the therapeutic product can be adjusted accordingly to manufacture dosages in variably desired strengths, i.e., light strength, regular strength, and extra strength.

During the method for producing the therapeutic product, if flavorings are desired, organic materials or organic extracts can be added to the mixing process in predetermined amounts to create the desired flavoring effects. Examples of flavorings include vanilla, chocolate, strawberry, cherry, menthol, and so forth.

Figure 6:
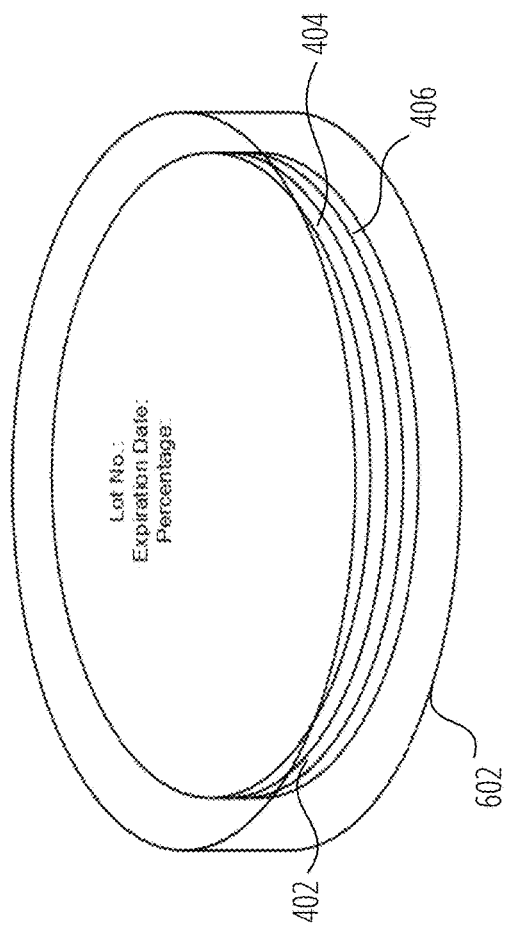
FIG. 6 illustrates a therapeutic product that includes a therapeutic portion, fibrous portion, and package, according to an example embodiment.

FIG. 6 illustrates a therapeutic product 600, according to an example embodiment. The therapeutic product 600 may include a fibrous portion 402 and a first subportion 404 and a second subportion 406 of a therapeutic portion structurally attached to the fibrous portion 402 to form the individual dose of the therapeutic product 600. The therapeutic product 600 may further include a package 602 configured to accommodate the fibrous portion 402 and the first subportion 404 and the second subportion 406 of the therapeutic portion attached to the fibrous portion 402.

Figure 7:
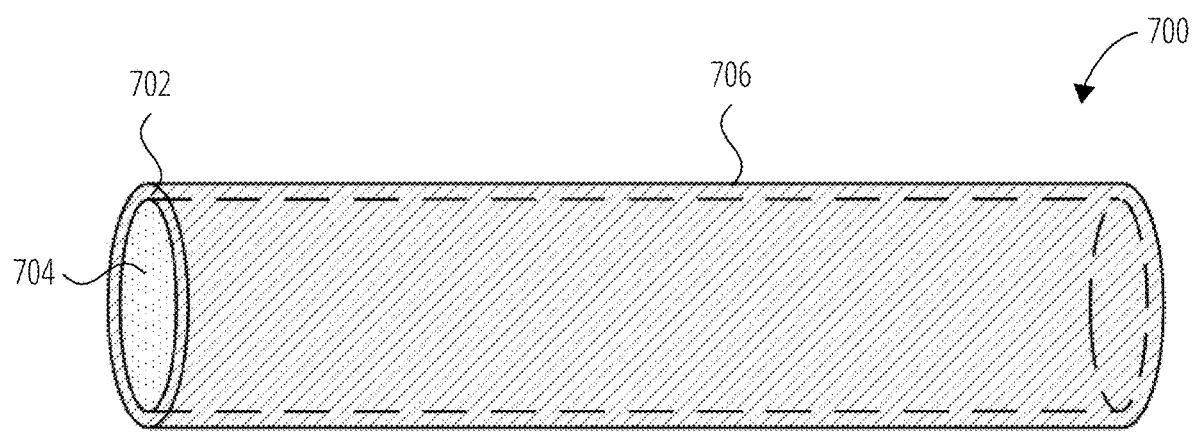
FIG. 7 illustrates a therapeutic product, according to an example embodiment.

FIG. 7 illustrates a therapeutic product 700, according to an example embodiment. The therapeutic product 700 may include a fibrous portion 702 and a therapeutic portion 704. The fibrous portion 702 may be provided in the form of a tube 706. The therapeutic portion 704 may be formed into tube 706 to provide an individual dose in the form of a tube 706 filled with the therapeutic portion 704.

Figure 8:
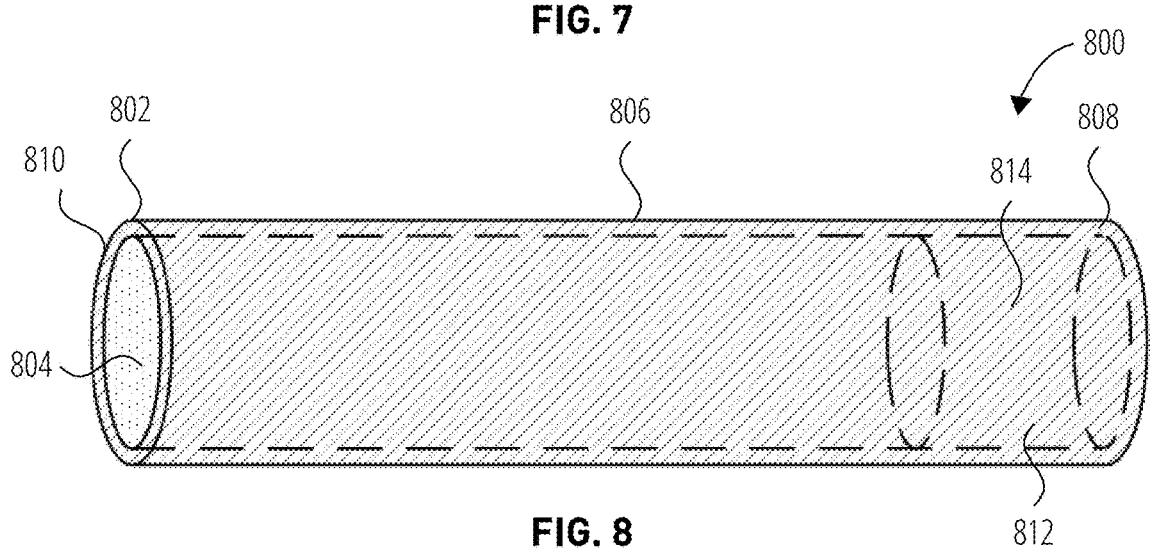
FIG. 8 illustrates a therapeutic product, according to an example embodiment.

FIG. 8 illustrates a therapeutic product 800, according to an example embodiment. The therapeutic product 800 may include a fibrous portion 802 and a therapeutic portion 804. Fibrous portion 802 may be provided in the form of tube 806. The therapeutic portion 804 may be extruded into tube 806 to provide an individual dose in the form of a tube 806 filled with the therapeutic portion 804. Tube 806 may have a first end 808 and a second end 810. Fibrous portion 802 may further include filter 812 made of the same material as the fibrous portion 802. Filter 812 may occupy space 814 at the first end 808 inside tube 806. In an example embodiment, filter 812 can be made as a fine or course cellulose lattice as is necessary for the filtration purposes.

In the embodiments shown in FIG. 7 and FIG. 8, the fibrous portion may be structurally attached to the therapeutic portion to form a cigarette.

Figure 9:
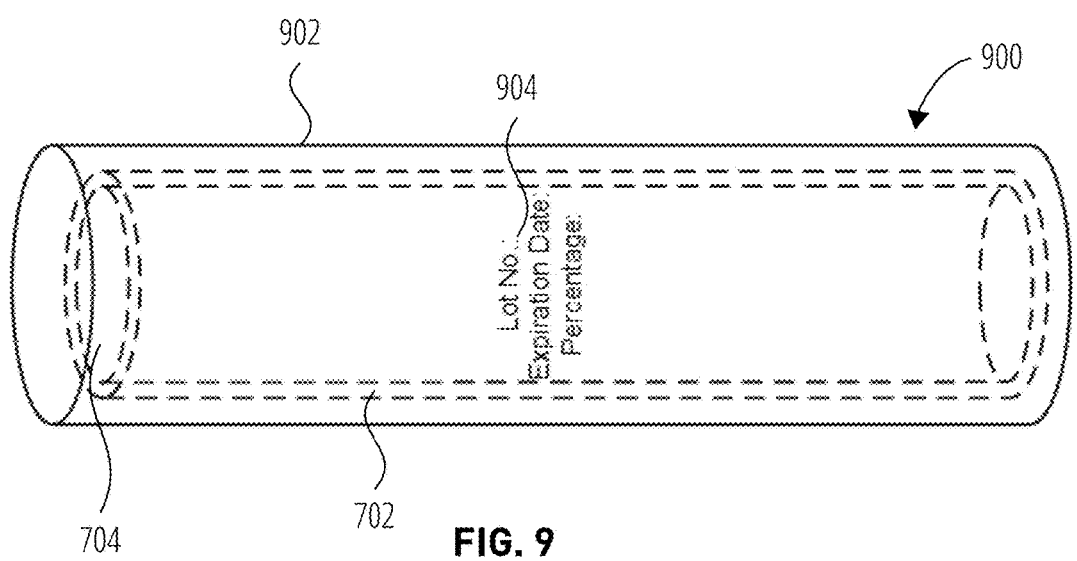
FIG. 9 illustrates a therapeutic product, according to an example embodiment.

FIG. 9 illustrates a therapeutic product 900, according to an example embodiment. The therapeutic product 900 may include a fibrous portion 702 provided in the form of a tube and a therapeutic portion 704 extruded into the fibrous portion 702. The therapeutic product 900 may further include a package 902 for accommodating the therapeutic portion 704 structurally attached to the fibrous portion 702.

The package 902 may be marked with one or more markings 108. The marking 108 may be similar to those described with reference to FIG. 1B.

FIGS. 10-13 illustrate a package of a therapeutic product 100, according to example embodiments. In general, the therapeutic product 100 may be packaged into blister packs, prescription bottles, or other applicable methods for containing and distributing therapeutic agents in a capsule/tablet/cigarette form. Moreover, the therapeutic product 100 does not need a dispenser for administering an individual dose as the individual dose is contained in a blister pack, bottle, or other applicable means of distribution.

Figure 10:
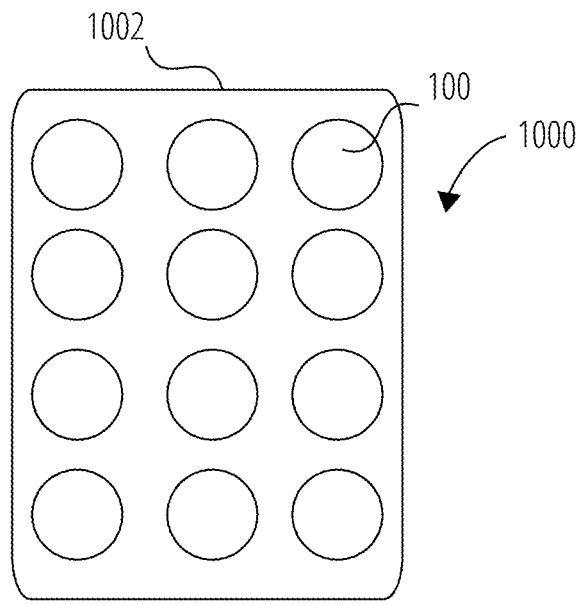
FIG. 10 shows a package in the form of a blister pack, according to an example embodiment.

FIG. 10 shows a package 1000 in the form of a blister pack 1002, according to an example embodiment. The blister pack 1002 may be a geometrically shaped blister pack of a plurality of individual doses of the therapeutic product 100. The blister pack 1002 may accommodate a plurality of therapeutic products 100, each located in an individual cell of the blister pack 1002.

Figure 11:
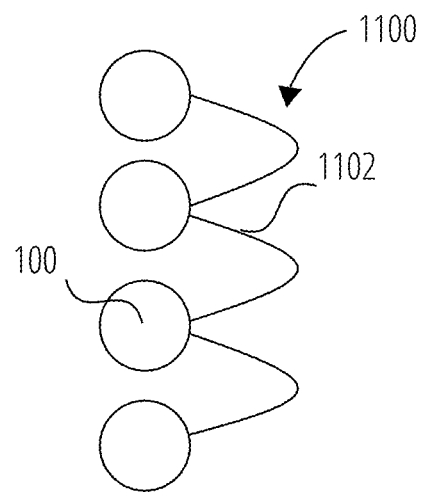
FIG. 11 illustrates a package in the form of a plurality of daisy-chained individual doses of a therapeutic product, according to an example embodiment.

FIG. 11 illustrates a package 1100 in a form of a plurality of daisy-chained individual doses 1102 of the therapeutic product 100, according to an example embodiment. In some embodiments, the package may be provided in a form of a roll of a plurality of daisy-chained individual doses 1102 of the therapeutic product 100.

Figure 12:
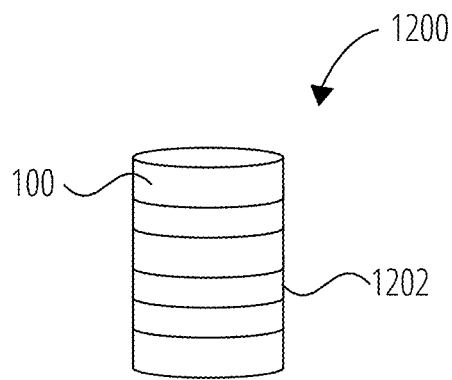
FIG. 12 illustrates a package in the form of a multi-column refill pack of a plurality of individual doses of a therapeutic product, according to an example embodiment.

FIG. 12 illustrates a package 1200 in the form of a multi-column refill pack 1202 of a plurality of individual doses of the therapeutic product 100, according to an example embodiment. In the multi-column refill pack 1202, the plurality of individual doses of the therapeutic product 100 may be stacked one upon the other.

Figure 13:
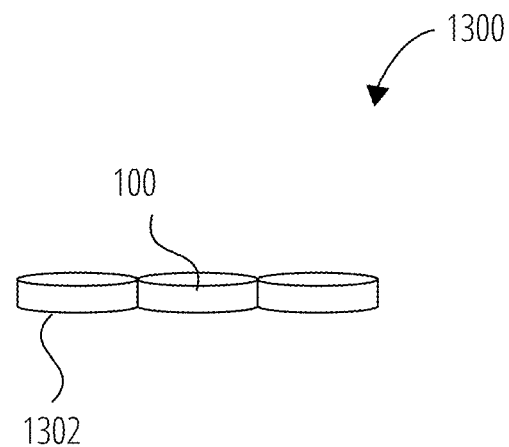
FIG. 13 illustrates a package in the form of a multi-row refill pack of a plurality of individual doses of a therapeutic product, according to an example embodiment.

FIG. 13 illustrates a package 1300 in the form of a multi-row refill pack 1302 of a plurality of individual doses of the therapeutic product 100, according to an example embodiment. In the multi-row refill pack 1302, the plurality of individual doses of the therapeutic product 100 may be connected to each other by their sides to create a row of the therapeutic products 100.

Figure 14:
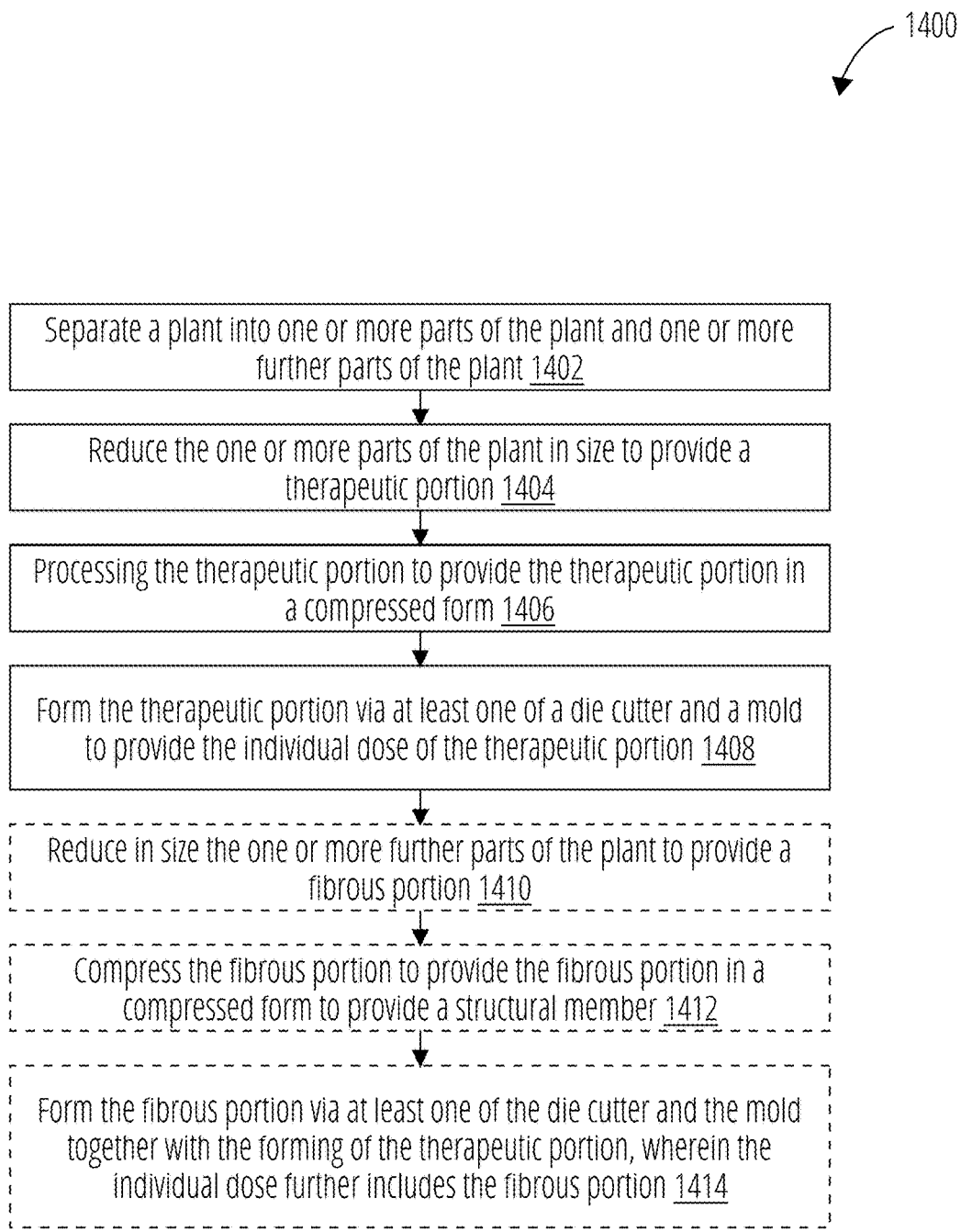
FIG. 14 is a flow chart of a method for producing a therapeutic product in the form of an individual dose for consumption, according to an example embodiment.

FIG. 14 is a flow chart of method 1400 for producing a therapeutic product in the form of an individual dose for consumption, according to an example embodiment. In some embodiments, the operations may be combined, performed in parallel, or performed in a different order. Method 1400 may also include additional or fewer operations than those illustrated.

Therapeutic agents contained in a plant (e.g., cannabis) are usually contained in non-fibrous portion of the plant. Specifically, the therapeutic agents from the cannabis plant can be found in the resin (a sticky substance secreted by trichomes of a cannabis plant), kief (accumulated trichomes, or resin glands, sifted from cannabis flowers through a sieve), and portions of the leaf material of the plant. The fibrous portion of the plant is everything remaining after the resins and other portions rich in therapeutic agents have been removed. The fibrous portion is the stem, branches, and leaves not containing therapeutic agents and is also referred to as hemp.

The method 1400 may commence in block 1402 with separating a plant into one or more parts of the plant and one or more further parts of the plant. The plant may include cannabis, tobacco, and a combination of the cannabis and the tobacco. The combination of cannabis and tobacco may additionally include a flavoring additive to provide a flavored combination of cannabis and tobacco. Cannabis used for producing the therapeutic product may be cultivated in a controlled and regulated environment and may be traced by a chain of custody to ensure the purity and contents of the raw product (the plant). Thus, only materials organic to the cannabis and/or tobacco plants and no foreign materials are present in the finished therapeutic product.

In an example embodiment, the separating of the plant may include separating flowers and leaves from the plant and separating the stem and branches from the plant. The flowers and the leaves constitute one or more parts of the plant used for forming the therapeutic portion. The stem, the branches, and leaves containing no resin constitute one or more further parts of the plant used for forming the fibrous portion. Thus, the flower and leaf material (which constitute the therapeutic portion) from the cannabis plant and/or tobacco plant, respectively, is separated from the stem and branches (which constitute non-therapeutic fibrous portion) of the plant. Upon being separated, the therapeutic portion and the fibrous portion may be collected separately for further use in the manufacturing process.

The therapeutic portion of the plant may be reduced in size by mechanical methods to provide a uniform distribution of therapeutic agents within the mass of the material. The therapeutic portion may include purely cannabis (flower/resin), cannabis extract (shisha), flavored cannabis, tobacco, a tobacco and cannabis combination, or a flavored cannabis and tobacco combination. Specifically, in block 1404, method 1400 may proceed with reducing one or more parts of the plant in size to provide a therapeutic portion. In block 1406, method 1400 may include processing the therapeutic portion to provide the therapeutic portion in a compressed form. In block 1408, method 1400 may proceed with forming the therapeutic portion via at least one of a die cutter and a mold to provide the individual, regulated dose of the therapeutic portion.

The fibrous portion of the plant may be reduced in size by similar mechanical methods to form a uniform distribution of a fibrous material within the mass of the material for use as a structural and binding agent for the therapeutic agents. Specifically, method 1400 may optionally include reducing, in block 1410, the one or more further parts of the plant in size to provide a fibrous portion. In an example embodiment, the reducing of the one or more parts in size and the reducing of the one or more further parts in size can be performed by grinding the one or more parts and grinding the one or more further parts. In some example embodiments, other mechanical methods for reducing a plant material in size can be used. In an example embodiment, reducing the one or more parts in size and reducing the one or more further parts in size may be followed by thrashing and/or pulverizing the one or more parts and the one or more further parts.

In an example embodiment, the therapeutic portion (i.e., the resinous portion of the plant) may be processed (e.g., by pressing or vibratory feed) and presented in a sheet form of the therapeutic portion. The therapeutic portion may be homogenous and uniform in consistency throughout the material and may be further formed into the therapeutic portion having a predetermined thickness for further providing to a die cutter or a mold. The therapeutic portion may then be compressed and formed into individual doses and presented for packaging.

In block 1412, method 1400 may optionally proceed with compressing the fibrous portion to provide the fibrous portion in a compressed form, which may act as a structural member for the therapeutic portion. In block 1414, method 1400 may optionally include forming the fibrous portion via at least one of the die cutter and the mold together with forming of the therapeutic portion. In an example embodiment, the forming of the therapeutic portion and the forming of the fibrous portion may include one of the following: extrusion, die cutting, mold forming, and the like.

In an example embodiment, two separate masses, i.e., the therapeutic portion and the fibrous portion, may be distributed from the hoppers/storages by gravity or other mechanical method and/or vibration at a predetermined and regulated rate so as to control the amounts of the therapeutic portion and the fibrous portions that acts as a structural binding agent for the therapeutic portion. The two separate masses may be then re-incorporated with each other (either by creating a substrate of the fibrous portion and attaching the therapeutic portion to surfaces of the substrate (as shown in FIGS. 4 and 5) or by extruding the tube of the fibrous portion and extruding or co-extruding the therapeutic portion inside the tube (as shown in FIGS. 7-9)) and formed into individual doses according to the predetermined therapeutic portion/fibrous portion ratio required to produce therapeutically measured, regulated, and structurally self-supported individual doses. The ratio of the therapeutic portion and the fibrous portion may be selected based on predetermined criteria.

As used herein, the term "self-supported" means that the fibrous portion of the plant is used to create a support for the therapeutic portion of the plant in the therapeutic product. The support may be in the form of a substrate or an internal substrate to which the therapeutic portion is attached (FIGS. 4 and 5) or an external cylinder within which the therapeutic portion is accommodated (FIGS. 7-9). In an example embodiment, the therapeutic portion can be presented with no substrate attached.

The fibrous portion may be used to provide the maximum surface area of the therapeutic portion. For example, the fibrous portion may be provided in the form of a substrate of a predetermined thickness and a predetermined shape (e.g., in a pancake-like form) and then the therapeutic portion may be attached to both sides of the substrate. As the thickness of the substrate may be much smaller than the width and the length of the substrate, the substrate may have the maximum surface area to which the therapeutic portion may be attached.

In an example embodiment, the forming may include molding or extrusion of the therapeutic portion and the fibrous portion to form individual doses in form of compressed tablets for packaging into blister packs, bottles, containers, or other means of distribution. The molding may include distribution of the combined therapeutic and structural agents, i.e., the therapeutic portion and the fibrous portion, for presentation to a mold. The mold may accept the therapeutic portion and the fibrous portion and form them into individual dose tablets/capsules.

The extrusion may include introducing the therapeutic portion and the fibrous portion into a die cutter via a screw press, or other method, for presentation to a shear, or rotary knife as the material exits the die cutter, to be cut at predetermined regulated and controlled intervals so as to produce a therapeutically measured, regulated, and structurally self-supported individual dose.

Upon the forming, the individual dose of the therapeutic product may include the therapeutic portion and the fibrous portion. Using only the therapeutic portion and the fibrous portion of the plants, without introducing any foreign materials, keeps the final therapeutic product organic to the original plants, with the exception of other intended organic material and possible flavorings. Therefore, method 1400 is based on the "whole plant" concept of providing the therapeutic product, in which the plant is used entirely and no portions of the plant are wasted.

In an example embodiment, the fibrous portion may be formed by weaving and pressing the fibrous portion to provide a woven substrate having a predetermined thickness and a predetermined form (e.g., round, rectangular, oval, and so forth). The woven substrate may have a top surface and a bottom surface. Method 1400 may further include attaching a first subportion of the therapeutic portion to the top surface of the woven substrate and attaching a second subportion of the therapeutic portion to the bottom surface of the woven substrate. The therapeutic material of the therapeutic portion may be attached to the fibrous substrate to produce an individual dose with a maximum surface area.

In an example embodiment, the fibrous portion may be formed in the form of a mesh (e.g., a basket weave), which may be used as a skeleton for attaching the therapeutic portion. For example, the therapeutic portion may be either pressed or adhered to the outside of the fibrous portion on both sides.

In an example embodiment, the forming of the fibrous portion may include forming the fibrous portion to provide a tube. In this embodiment, the forming of the therapeutic portion may include inserting or installing the therapeutic portion into the tube. The extrusion of the fibrous portion and the extrusion of the therapeutic portion may be performed concurrently. The tube may be cut to provide a tube having a predetermined length. Thus, upon forming of the fibrous portion and the therapeutic portion, the therapeutic product may be provided in a form similar to a cigarette.

The method 1400 may further include forming a further portion of the fibrous portion to provide a filter made of the fibrous portion. The tube may have a first end and a second end. Method 1400 may further include inserting the filter into a space at the first end inside the tube. Thus, method 1400 may result in forming a tube (i.e., a cylinder) made of the fibrous portion with a plug acting as a filter at one end of the tube and made of the fibrous portion. Thus, the tube made of the fibrous portion remains with the therapeutic portion in the final therapeutic product and is not used solely for forming and then separated from the therapeutic portion as in conventional methods of manufacturing the therapeutic products.

In an example embodiment, the filter may be not inserted inside of the tube, but may be made in the form of a cap placed onto one end of the tube.

In an example embodiment, prior to die cutting/mold forming of individual doses, the homogeneous sheet of the therapeutic portion (which contains the cannabis resin) may be evaluated for content and strength. The therapeutic portion may also be mixed with additives allowed by the regulations to be present in cannabis products, such as pharmaceutical products, flavors, and/or tobacco.

Once the individual dose is pressed and returned from the die cutter or the mold, individual doses may be presented for packaging into an individual, strip, or multi-pack package for mass distribution. The package may include various embodiments, for example, individually wrapped doses/servings, "ticket roll" packages enabling a user to purchase multiple individually wrapped servings connected/"daisy chained" together, a multi row/column blister pack, a blister styled multi-pack geometrically designed to fit an end user device for consumption, and so forth.

Thus, the method 1400 may result in providing a therapeutic product in a form of an individual dose/serving of cannabis, tobacco, a cannabis and tobacco mixture, and a flavored cannabis and tobacco mixture derived from a known source, and labeled for consumer use, delineating notes, cautions, warnings, dosing, strength, type, and percentage of therapeutic agents and nicotine in the therapeutic product. The method 1400 may further result in providing a package of a plurality of therapeutic products in a form of individual doses of cannabis, tobacco, cannabis and tobacco mixtures, and flavored cannabis and tobacco mixtures. The example package may include individually connected servings of the therapeutic product "daisy chained" in a roll, multi-column or multi-row refill packs, and geometrically shaped blister-style packs designed for use in commercially available end user devices.

Figure 15:
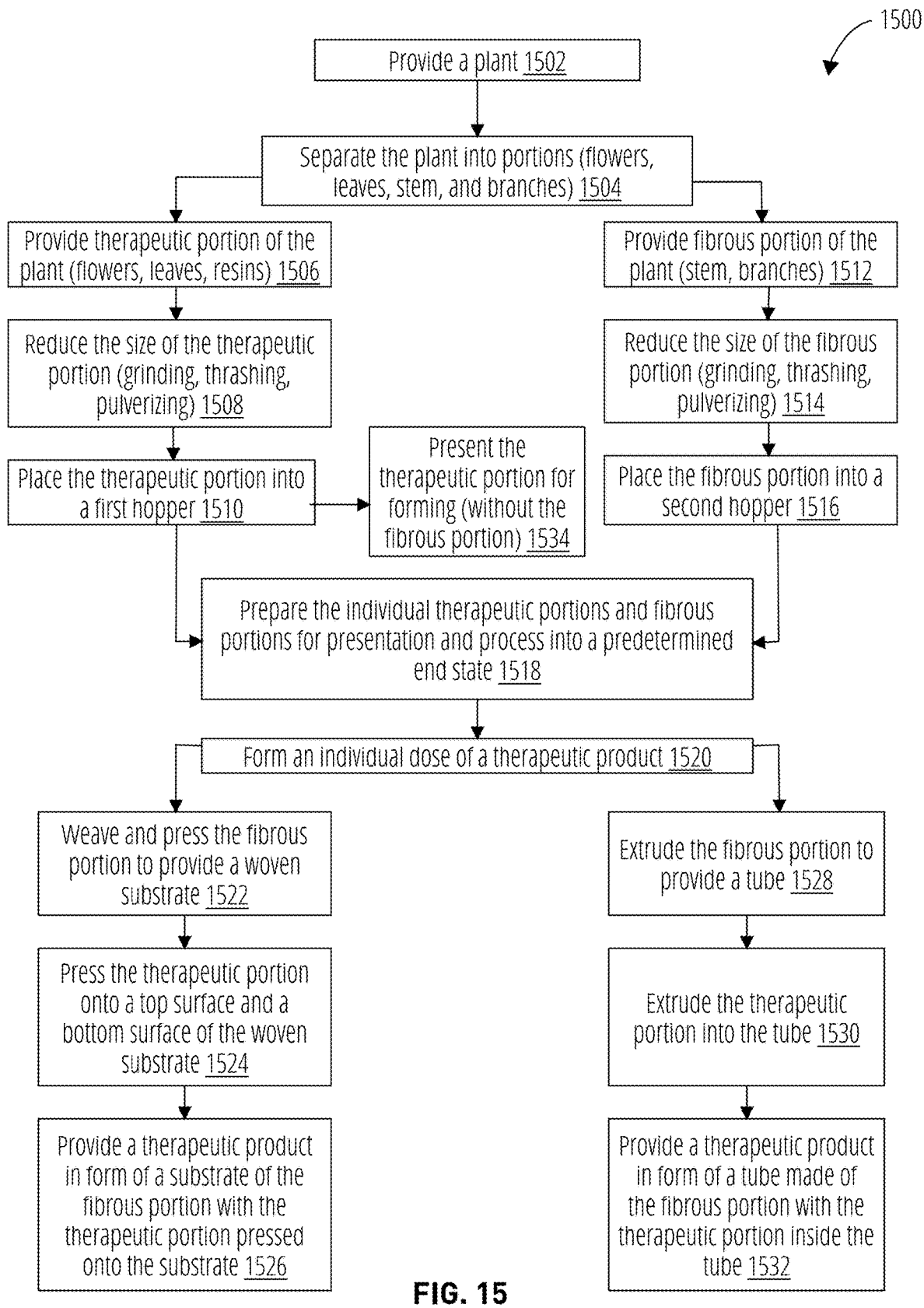
FIG. 15 is a flow chart of a method for producing a therapeutic product in the form of an individual dose for consumption, according to an example embodiment.

FIG. 15 is a flow chart of method 1500 for producing a therapeutic product in the form of an individual dose for consumption, according to an example embodiment. Method 1500 may commence with providing a plant in block 1502. Method 1500 may proceed with separating the plant into portions (such as flowers, leaves, stem, and branches) in block 1504. Upon separating of plant into portions, the portions may be divided into a therapeutic portion of the plant (flowers, leaves, resins) provided in block 1506 and a fibrous portion of the plant, i.e., the hemp (stem, branches) provided in block 1512.

Upon providing the therapeutic portion in block 1506, the method 1500 may proceed with reducing, in block 1508, the therapeutic portion in size, i.e., reducing the bulk mass of the therapeutic portion (e.g., by grinding, thrashing, pulverizing, chemical reduction, and so forth) to provide a form for the therapeutic portion suitable for further processing. In block 1510, the therapeutic portion may be placed into the first hopper.

Upon providing the fibrous portion in block 1512, the method 1500 may proceed with reducing the fibrous portion in size, i.e., reducing the bulk mass of the fibrous portion (e.g., by chemical or mechanical means, which may include grinding, thrashing, pulverizing, chemical reduction, and so forth) in block 1514. In block 1516, the fibrous portion may be placed into a second hopper.

Upon placing the therapeutic portion into the first hopper and placing the fibrous portion into the second hopper, the method 1500 may proceed with preparing the individual therapeutic portions and fibrous portions for presentation (e.g., by simultaneously distributing the therapeutic portion from the first hopper and the fibrous portion from the second hopper at a predetermined rate for initial forming of the individual therapeutic portions and fibrous portions) and processing into the predetermined end state in block 1518. In block 1520, an individual dose of a therapeutic product may be formed.

In an example embodiment of method 1500, the individual dose of the therapeutic product may be formed as follows. In block 1522, the fibrous portion may be formed to provide a woven substrate. In block 1524, the therapeutic portion may be attached to the top surface and bottom surface of the woven substrate. Upon attaching the therapeutic portion and the fibrous portion, a therapeutic product in form of a substrate of the fibrous portion with the therapeutic portion attached to the substrate may be provided in block 1526.

In an example embodiment of method 1500, the individual dose of the therapeutic product may be formed as follows. In block 1528, the fibrous portion may be extruded to provide a tube. In block 1530, the therapeutic portion may be extruded into the tube. Upon extruding the fibrous portion and the therapeutic portion, a therapeutic product in form of a tube made of the fibrous portion with the therapeutic portion inside the tube may be provided in block 1532.

In an example embodiment of the method 1500, upon placing the therapeutic portion into the first hopper in block 1510, the therapeutic portion may be solely presented for forming into the individual dose of the therapeutic product (without the fibrous portion) in block 1534.

Figure 16:
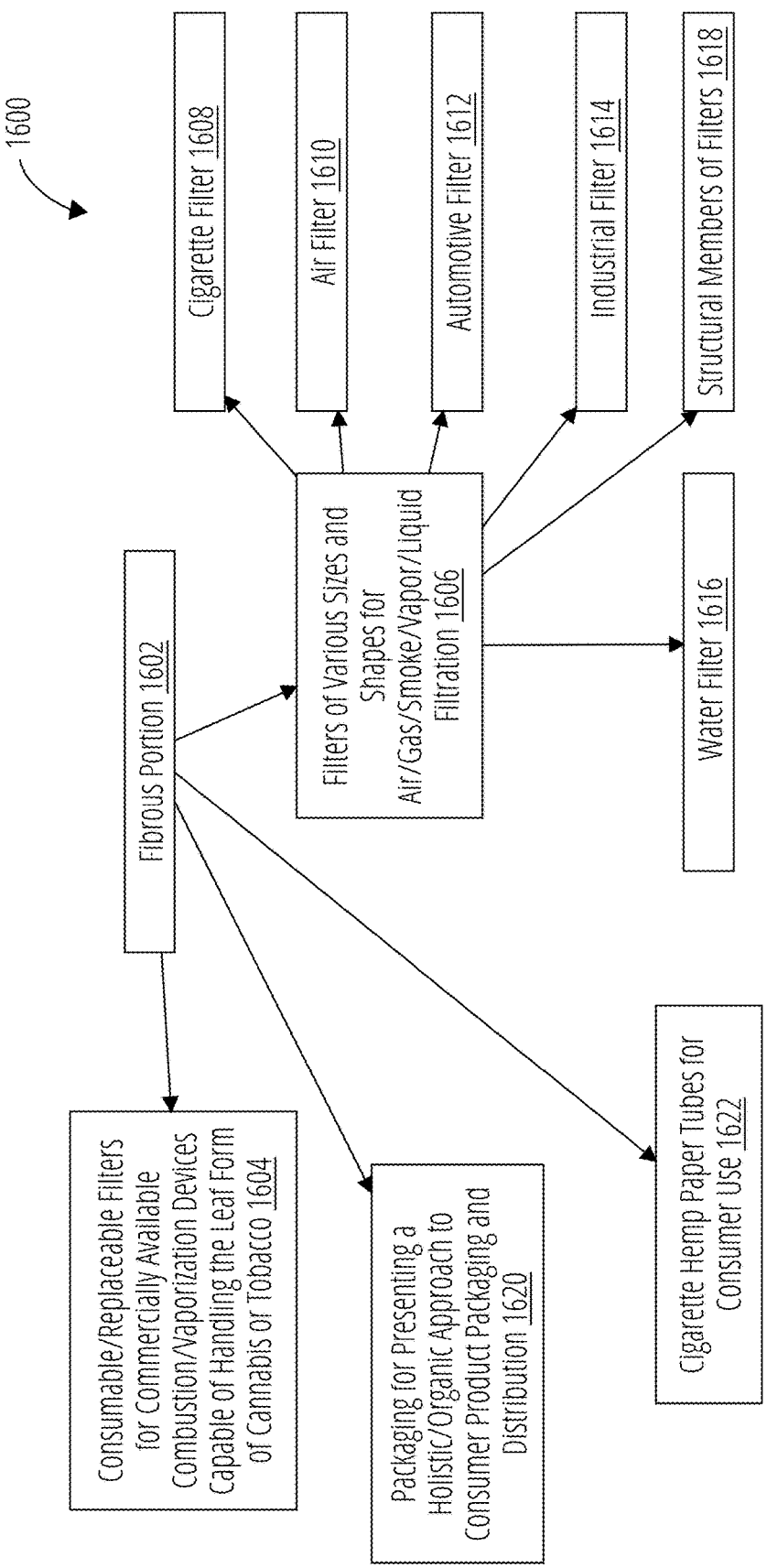
FIG. 16 illustrates the use of a fibrous portion of a plant, according to an example embodiment.

FIG. 16 illustrates the use 1600 of a fibrous portion of a plant, according to an example embodiment. After separating the plant into the therapeutic portion and the fibrous portion shown in block 1602, the fibrous portion may be reduced in size and stored for further processing and use. The fibrous portion of the plant remaining after the resinous portions of the plant are removed may be processed for use as consumable/replaceable filter media for commercially available combustion/vaporization devices capable of handling the leaf form of cannabis or tobacco, as shown in block 1604.

In example embodiments, the fibrous portion, i.e., the hemp, may be used for creating filter media of various sizes and shapes for air/gas/smoke/vapor/liquid filtration, as shown in block 1606. The filter media can be used for all types of filtration applications, e.g., cigarette filters 1608, air filters 1610, automotive filters 1612, industrial filters 1614, water filters 1616, structural members 1618 of filters, and the like.

In example embodiments, the fibrous portion may be formed into a package for presenting a holistic/organic approach to consumer product packaging and distribution, as shown in block 1620. In further example embodiments, the fibrous portion may be formed into hemp cigarette paper tubes for consumer use, as shown in block 1622.

Thus, therapeutic products in a form of individual doses for consumption and methods for producing a therapeutic product in a form of an individual dose for consumption have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A blister pack of hemp within a filter comprised of cellulose lattice which also includes a fibrous portion which includes a tube with a basket weave and wherein the tube has a cap on either end of the tube, wherein the fibrous portion is formed by weaving and pressing the fibrous portion to provide a woven substrate having a predetermined thickness and a predetermined form wherein the woven substrate has a top surface and a bottom surface and wherein attaching a first subportion of the hemp to the top surface of the woven substrate and attaching a second subportion of the hemp to the bottom surface of the woven substrate.

* * * * *